United States Patent
Goldmann et al.

[11] Patent Number: 6,053,938
[45] Date of Patent: Apr. 25, 2000

[54] TEXTILE VESSEL PROSTHESIS, PROCESS FOR ITS PRODUCTION AND APPARATUS FOR ITS PRODUCTION

[75] Inventors: Helmut Goldmann; Helmut Waldert, both of Melsungen, Germany

[73] Assignee: Aesculap AG & Co. KG, Tuttlingen, Germany

[21] Appl. No.: 08/517,497

[22] Filed: Aug. 21, 1995

[30] Foreign Application Priority Data

Aug. 27, 1994 [DE] Germany .............................. 44 30 485

[51] Int. Cl.$^7$ ...................................................... A61F 2/06
[52] U.S. Cl. ........................................................... 623/1
[58] Field of Search ................................................ 623/1, 12

[56] References Cited

U.S. PATENT DOCUMENTS

| | | | |
|---|---|---|---|
| 2,836,181 | 5/1958 | Tapp | 623/1 X |
| 3,736,646 | 6/1973 | Schmitt et al. | 29/458 |
| 3,867,190 | 2/1975 | Schmitt et al. | 117/138.8 |
| 3,945,052 | 3/1976 | Liebig . | |
| 4,033,938 | 7/1977 | Augurt et al. | 260/78.3 R |
| 4,047,252 | 9/1977 | Liebig et al. . | |
| 4,243,775 | 1/1981 | Rosensaft et al. | 525/415 |
| 4,300,565 | 11/1981 | Rosensaft et al. | 128/335.5 |
| 4,441,215 | 4/1984 | Kasfer . | |
| 4,441,496 | 4/1984 | Shalaby et al. | 128/335.5 |
| 4,653,497 | 3/1987 | Bezwada et al. | 128/335.5 |
| 4,700,704 | 10/1987 | Jamiolkowski et al. | 128/335.5 |
| 4,705,820 | 11/1987 | Wang et al. | 524/381 |
| 5,320,624 | 6/1994 | Kaplan et al. | 606/77 |
| 5,413,597 | 5/1995 | Krajicek | 623/1 |
| 5,468,253 | 11/1995 | Bezwada et al. | 606/230 |
| 5,653,746 | 8/1997 | Schmitt | 623/1 |

FOREIGN PATENT DOCUMENTS

| | | |
|---|---|---|
| 0 108 171 | 10/1982 | European Pat. Off. . |
| 0 391 586 | 3/1990 | European Pat. Off. . |
| 0 608 139 | 7/1994 | European Pat. Off. . |
| 2334488 | 4/1976 | France . |
| 24242 | 11/1962 | Germany . |
| 2255743 | 11/1972 | Germany . |
| 160857 | 4/1984 | Germany . |
| 1507369 | 9/1989 | U.S.S.R. ..................................... 623/1 |
| 2 033 411 | 5/1980 | United Kingdom . |
| 8201647 | 5/1982 | WIPO . |

OTHER PUBLICATIONS

"Entwicklung einer textilen Arterienprothese mit faserforminger Stuckur," by Dimplom–Ingenieur Heinrich Planck, published at University of Stuttgart (submitted Jul. 25, 1979) with English–language translation "The Development of a Textile Arterial Prosthesis with Fibre–like Structure." (2 pages).

P.F. Nockemann, "Suture Materials—General Part," *Surgical Suture*, 3d ed. (1980) p. 42.

Ray et al., "Polydioxanone (PDS), A Novel Monofilament Synthetic Absorbable Suture," *Surgery, Gynecology & Obstetrics*, (1980) vol. 153.

Katz et al., "A New Synthetic Monofilament Absorable Suture Made From Polytrimethylene Carbonate," *Surgery, Gynecology & Obstetrics* (1985) vol. 161.

*Primary Examiner*—David H. Willse
*Attorney, Agent, or Firm*—Pennie & Edmonds LLP

[57] ABSTRACT

The invention relates to a conical, textile vessel prosthesis made from textile material transformed by elastic expansion and fixing and/or by the shrinkage of shrinkable wall material, starting from a cylindrical tubular fabric, into a conical shape. The prosthesis preferably has a pleating.

4 Claims, 1 Drawing Sheet

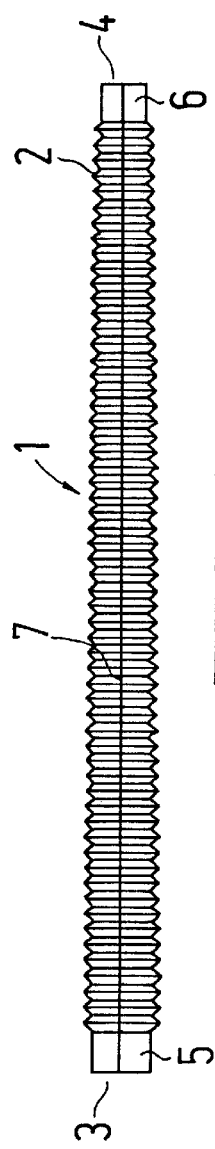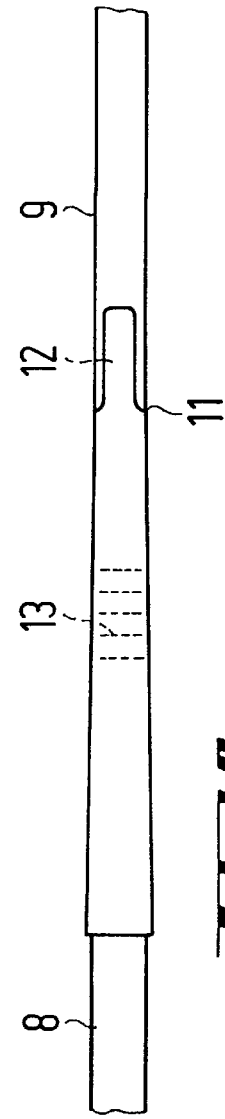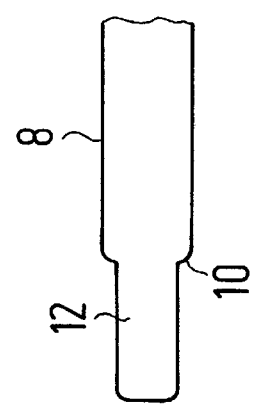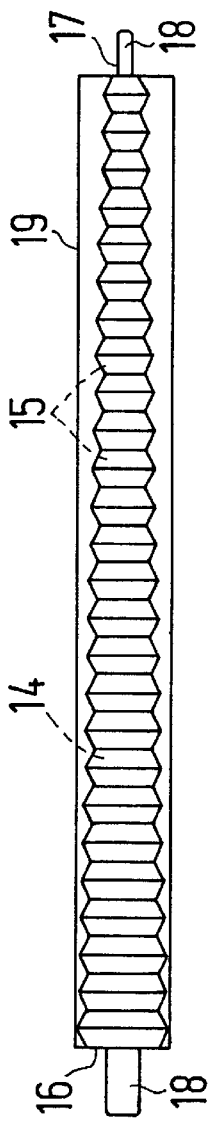

TEXTILE VESSEL PROSTHESIS, PROCESS FOR ITS PRODUCTION AND APPARATUS FOR ITS PRODUCTION

FIELD OF THE INVENTION

The invention relates to a textile, particularly knitted or woven, conical vessel prosthesis, a process for its production and apparatuses for its production.

BACKGROUND OF THE INVENTION

Artificial vessel prostheses for replacing blood vessels and other hollow organs of the human or animal body are known. Thus, there are knitted vessel prostheses, cf. DE-A-24 61 370, U.S. Pat. No. 3,945,052 and U.S. Pat. No. 4,047,252, as well as woven prostheses, cf. EP-B1-108 171. The prostheses can have a smooth surface and can be in the form of a single or double velour, as is apparent from the above documents. In addition, the prostheses can have a so-called bifurcation, i.e. a forking into generally two thinner branches. The known prostheses comprise cylindrical tubular portions with a constant diameter, apart from a diameter reduction as a result of the bifurcation. The prostheses can also be corrugated or ribbed, which is generally referred to in the art as pleating. The prostheses can be impregnated with a resorbable or non-resorbable sealing medium for the sealing of the textile wall structure. They can also be used in the unimpregnated state and during the operation there is at least a precoagulation of the prosthesis wall with the blood of the patient, in order to bring about the necessary sealing until the weave has grown into the wall structure.

In order to obtain favourable flow conditions, vessel prostheses can be given a conical configuration in much the same way as natural blood vessels. Such a conical vessel prosthesis of non-textile material and the production thereof is described in EP-A2-391 586. For the production thereof a polytetrafluoroethylene, extruded tubular fabric is initially stretched to 2 to 6 times its original length and becomes porous. This is followed by an expansion of the porous tubular fabric by an expanding engaging or pushing onto a conical mandrel, which is ultrasonically excited. A similar non-textile, conical vessel prosthesis is described in East German patent 160857. Textile vessel prostheses with a stepped diameter are also commercially available, without details of their manufacturing procedure being known. Such prostheses are also incorrectly called conical. DE-OS 22 55 743 discloses a textile vessel prosthesis with different diameters at its ends and which is conically constructed in the longitudinal direction. The vessel prosthesis is produced by generally known knitting methods. In particular, it is produced on a fine pitch flat knitting machine with a number of needles corresponding to the required inside width or diameter. The stitches or loops are successively removed and placed in inactive needles, so that at the end the inside width corresponds to the requisite inside width of the prosthesis.

Another textile vessel prosthesis with diameter variation is known from the publication PLANCK, HEINRICH: Development of a textile arterial prosthesis with fibrous structure (in German), Stuttgart University thesis, 1980, p 38. The diameter variation is brought about in that with the aid of additional binding threads the free inside diameter of the knitted tubular prosthesis is adjusted and conical prostheses can be produced using the same procedure.

SUMMARY OF THE INVENTION

The problem of the invention is to provide a textile, conical vessel prosthesis, which is able to offer the variation and design possibilities of the hitherto known textile vessel prostheses. The object of the invention is a knitted or woven vessel prosthesis with a conical construction in the longitudinal direction and which, apart from any bifurcations, has a constant number of yarns or threads in cross-section over the entire length. The term conical construction in the longitudinal direction means a constant amount diameter change, which is preferably continuous over the prosthesis length.

The prosthesis according to the invention can be knitted or woven, as a function of the demands made thereon. The standard textile materials can be used, preference being given to polyester and polypropylene materials. Generally the prosthesis is made from multifilament yarns, which can be smooth or textured. Particularly in the case of woven prostheses, at least in part the yarns can be highly shrinkable and further reference will be made to this hereinafter.

According to the invention, starting from a prosthesis blank produced in known manner as a cylindrical, tubular fabric, the conical form is produced during the making up of the prosthesis. It is necessary for the number of yarns in the cross-section of the prosthesis to be constant over the entire length, despite the conical construction. This means that in the case of knitted prostheses the number of loops or wales is constant over the prosthesis length and with woven or braided prostheses correspondingly the number of yarns is in cross-section constant over the entire length. The conicity can be formed by elastic expansion and fixing and/or shrinking shrinkable wall material, starting from the cylindrical tubular fabric.

The conicity of the prosthesis is preferably linear over its entire length, i.e. it is uniformly constructed. The diameter difference from one end to the other of the prosthesis can be 10 to 100%, particularly 30 to 50%, based on the smaller diameter. The prosthesis length can be 10 to 100 cm. Generally these are standardized lengths of 40 to 60 cm and in particular 40 or 60 cm. The length relates to the tubular fabric length without any pleating and which can also be provided and is preferred according to the invention. Also in the case of pleated prostheses the conicity is as in the case of unpleated prostheses, the corrugated or folded structure being superimposed on the conical path. The pleating generally represents 15 to 40, particularly 20 to 30 corrugations or folds per 100 mm of stretched prosthesis.

In the case of the conical prosthesis according to the invention, in the case of thread or yarn material, in the vicinity of the large diameter prosthesis end, compared with the thread or yarn material in the vicinity of the small diameter prosthesis end, there is preferably no stretching or elongation of the yarn or thread material. As a result the tensile strengths of the fibres or threads and the bursting pressure of the prosthesis is substantially constant over its length. If the larger diameter is brought about by expanding the tubular fabric, then the expansion is limited to a widening or reorientation of the yarn bond or loop, without there being any lengthening or expansion of the actual thread or fibre material. As a result of the reorientation of the meshes or bonds and weaves the porosity of the textile wall of the prosthesis can be significantly larger in the vicinity of the larger diameter, as a function of the expansion percentage, starting roughly in the prosthesis centre, than in the vicinity of the thin end, without this greater porosity having a disadvantageous effect. Both in the case of a precoagulation and an impregnation the porosity differences have no effects. The same occurs in another embodiment of the invention in which the smaller diameter at the thinner end of the prosthesis is formed by shrinking shrinkable yarns, starting from a tubular fabric, whose diameter corresponds to the diameter at the larger end. In this embodiment the porosity at the thinner end, once again starting roughly in the prosthesis centre, is significantly smaller than at the larger diameter end. Embodiments are also conceivable starting with a tubular fabric, which roughly corresponds to the average diameter and in which one half is expanded by expanding reorientation of the bond or weave and the other half is narrowed by increasing shrinkage.

The diameter value divergences from the desired value can be kept very small and are normally max±5%. The diameters can cover the standard range, which can be from 4 to 40 mm.

The process for the production of the conical prostheses according to the invention is characterized in that textile, particularly knitted or woven, tubular prosthesis blanks with a diameter which is constant over their length and substantially without lengthening the fibres or threads are transformed into a conical form and the conical form is fixed by heating to a temperature above the glass transition point and below the melting range of the fibrous material and subsequent cooling. The fixing is advantageously performed whilst the tubular prosthesis blanks are in the preferably stretched out state on a conical template. The application of the prosthesis blanks to the conical template preferably takes place without heat action.

Particularly knitted prosthesis blanks are used in the case of a preferred embodiment with a gauge or calibre, whose inner circumference corresponds to the circumference of the conical template at the smaller end or a marking provided there and on applying the prosthesis blanks to the template an elastic expansion takes place in the textile structure, particularly the stitches or loops, without any fibre or thread elongation. The elastic expansion can be fixed by heat action and retractive forces are reduced. The conical template can be constituted by a conical flat bar, whose circumference corresponds to the desired calibre of the finished, conical prosthesis.

If a pleating is desired, then the latter is preferably formed beforehand, when the prosthesis blank is located on the conical flat bar. For this purpose on either side of the conical flat bar transversely directed hot embossings can be made at intervals from one another in the tube wall and they form the subsequent depressions of the pleating. The transversely directed hot embossings need not cover the entire circumference of the prosthesis tube, even though this is normally the case. A partial prior formation of the depressions is adequate. According to a further development of the process according to the invention, despite the conical structure of the prosthesis drawn onto the conical flat bar, the size of the embossed strips is to be kept constant over the entire length. The expression end of the flat bar does not mean that the latter ends here. In this vicinity of the conical flat bar it is also possible to provide a marking or width step and a reduction of the width is preferred, because this also favours the application of clamping devices, which can be used for fixing the length of the prosthesis on the flat bar.

According to another embodiment of the process according to the invention, more particularly woven prosthesis blanks can be used with a calibre or gauge, whose inner circumference corresponds to the circumference of the conical template at the larger end. The prosthesis blanks drawn onto the conical template can then be shrunk onto the conical template utilizing the fibre shrinkage of shrinkable fibres and accompanied by a calibre reduction. In this embodiment the conical template is preferably constituted by a conical round bar. If here again a pleating is desired, then it is preferably formed beforehand at the same time as shrinking the calibre. For this prior formation it is appropriate to use conical templates in the form of round bars with transversely directed corrugations or ribs, whose spacings correspond to those of the pleating.

The formation of a pleating after producing the conical form by shrinkage on a conical flat bar using conventional processes by folding in prostheses is also possible.

The completion of the pleating can be carried out in that the conically formed or shaped prosthesis with the preformed pleating is shoved onto or engaged on a conical round bar, accompanied by the formation of a bellows and the conicity of said bar is steeper corresponding to the shortening caused by the bellows. This can be followed by a further fixing by heating in order to reduce retractive forces. After cooling the finished prosthesis with remaining pleating is removed. Its length is correspondingly smaller compared with the unpleated prosthesis. If the pleating of the prosthesis is pre-formed on a flat bar by embossing, then this is generally visible on the finished, not or not yet impregnated prosthesis in that when the prosthesis is stretched under considerable tension it is inclined to assume a flat shape corresponding to the position of the prosthesis on the flat bar.

Conical prostheses with bifurcations can be produced correspondingly. For this purpose separate templates and/or a correspondingly forked template can be used for the main, larger diameter tube and for the branched, smaller diameter tubes.

The invention also relates to an apparatus for producing the conical prosthesis, which is characterized in that a conical template is provided on which can be engaged a pre-formed, textile prosthesis blank without lengthening the thread or fibre material, the original inner circumference of the prosthesis blank and the circumference of the conical template at the larger or smaller end being so matched to one another that the inner circumference of the prosthesis blank corresponds to the circumference of the conical template in the area between the large end and the small end. In an embodiment the template is formed by a conical flat bar, whose circumference at the narrow end preferably corresponds to the inner circumference of the prosthesis blank. In another embodiment the template is formed by a preferably corrugated or ribbed, conical round bar, whose circumference at the larger end preferably corresponds to the inner circumference of the prosthesis blank.

BRIEF DESCRIPTION OF THE DRAWINGS

Further features and advantages of the invention can be gathered from the following description of preferred embodiments in conjunction with the drawings and subclaims. The individual features in the individual embodiments can be implemented singly or in combination with one another. In the drawings show:

FIG. 1 An embodiment of the conical prosthesis according to the invention.

FIG. 2 An apparatus for producing the prosthesis with a half-engaged prosthesis blank.

FIG. 3 Another apparatus for producing the prosthesis with a completely engaged prosthesis blank.

DETAILED DESCRIPTION OF THE PREFERRED EMBODIMENTS

The embodiment of the invention according to FIG. 1 shows a conical, textile vessel prosthesis 1, which is knitted from polyester yarn as a double velour tubular fabric. The tubular fabric originally had a length of 60 cm and has been shortened roughly to half by corrugated pleating 2 of the wall material. At one end 3 the prosthesis has a larger diameter corresponding to a calibre or gauge of 8 mm and at the other, smaller diameter end 4 the calibre or gauge is 6 mm. The conicity is uniformly linear from one end to the other, the diameter divergences being approximately 0.5%. The number of stitches or wales along the prosthesis circumference is constant from one end to the other, the stitch or loop size increasing somewhat from the smaller end 4 to the larger end 3. The end portions 5 and 6 at the ends 3 and 4 are substantially cylindrical and have no pleating. In the production of the prosthesis these end portions are used for mechanical fixing purposes. For example, following a possible impregnation with a resorbable or non-resorbable coating and/or making up, they are cut off prior to Sterilization. A characteristic line 7 in the form of black yarn material is knitted into the otherwise white prosthesis and is used to identify the orien tation of the prosthesis, also during the operation, so as to avoid any twisting and a consequently possible diameter reduction of the prosthesis during implantation.

FIG. 2 shows a conical template 8 for the conical expansion of a prosthesis blank 9, which is knitted as a tubular fabric having a constant diameter. The conical template is in the form of a coni cally tapered flat bar 8 with a wide end 10 and a narrow end 11 and on the ends there are stepped extension pieces 12. The tubular fabric of the prosthesis blank 9 has a calibre of 6 mm corresponding to an inner circumference of approximately 19 mm. Correspondingly the width and thickness of the flat bar 8 at the narrow end 11 is such that a roughly corresponding outer circumference is obtained. The template is used for expanding the prosthesis blank to a 8 mm calibre at the wide end. Correspondingly the width and thickness of the flat bar at the wide end are kept such that a circumference of approximately 25 mm is obtained. The engagement of the prosthesis blank 9 on the conical template 8 takes place at ambient temperature, accompanied by the elastic expansion of the loop structure of the knitted fabric. The engaged prosthesis blank 9 is somewhat longer than the conical portion of the template 8, so that its ends can be fixed to the extension pieces 12. In this position the conical shape of the prosthesis blank is fixed in order to reduce retractive forces. The fixing temperatures in the case of polyester are 80 to 200° C., particularly 150 to 180° C. and the fixing times are 24 hours to one minute, particularly 7 to 3 minutes. In the case of other materials the fixing conditions are chosen correspondingly, the temperature being above the glass transition point and below the melting range of the particular polymer. After fixing the conical shape it is possible to pre-form the pleating by embossing with the prosthesis blank still on the conical template. For this purpose on either side of the template parallel transverse strips 13 are embossed on the prosthesis blank wall. The embossed strips 13 are shown only in broken line form in FIG. 2, because they are only made following the conical expansion of the prosthesis blank 9. Embossing can take place at temperatures in the range 120 to 200° C., particularly 150 to 180° C. for a time of 5 minutes to 30 seconds and in particular 2 to 1 minute. The embossing pressure can vary within wide limits and preferably decreases with increasing prosthesis blank calibre. Thus, in the case of a prosthesis blank with a calibre of 6 mm the embossing pressure can be about 35 N/cm$^2$, whereas it is about 7 N/cm$^2$ for a calibre of 30 mm. The length of the embossed transverse strips 13 need not cover the entire prosthesis circumference. For practical reasons the length of the transverse strips L3 generally corresponds to the width of the flat bar 8.

FIG. 3 shows another embodiment of a conical template, which is in the form of a conical round bar 14, which has on its surface a slight corrugation or transverse ribs 15 for the pre-formation of the pleating. The template has a thick end 16 with a calibre or gauge 8 and a thin end 17 with a calibre or gauge 6, once again extension pieces 18 being provided on the ends.

Unlike in the embodiment according to FIG. 3 for the template 14 in the form of a round bar a prosthesis blank is provided, whose calibre corresponds to the calibre 8 of the thick end 16 of the template 14. The prosthesis blank 19 contains a proportion of fibrous material with high shrinkability, so that the prosthesis blank on heating and simultaneous fixing is shrunk onto the conical round bar 14 and as a result of the transverse ribs 15 of said round bar acquires a slight corrugation which leads to the pre-formation of the pleating.

As can be gathered from FIG. 3, it is also possible to use a prosthesis blank, whose calibre is roughly in the mid-range between that at the thin and thick ends, so that the prosthesis blank is partly brought into the conical shape by expansion and partly by shrinkage. The embodiment of FIG. 3 is particularly suitable for woven prostheses, which only have a limited elastic elongatability of the weave, without the fibres being elongated. Such woven prosthesis blanks are consequently generally used with a calibre corresponding to the thick end of the conical template, so that the conical shape is substantially exclusively obtained by shrinkage.

Following the removal of the prosthesis blanks from the conical template they can be engaged on conical round bars, whose length is reduced to approximately a quarter of the length of the original tubular fabric and which correspondingly have a more pronounced conicity. For practical handling the conical round bars are preferably kept longer and the desired calibres for the two ends of the prostheses are respected by corresponding markings on the round bar. On engaging the conically shaped prosthesis blank with pre-formed pleating, the prostheses blanks can be telescoped in accordion-like manner, accompanied by the formation of a bellows. In this position they once again undergo fixing and the fixing temperatures for polyester are generally between 140 and 180° C., particularly between 150 and 170° C. The fixing time is correspondingly between 2 hours and 10 minutes, particularly between 20 and 15 minutes. After removal the prosthesis maintains the conical shape and pleating.

The conical prostheses according to the invention can, if desired, be impregnated in per se known manner for sealing the loop structure. An impregnation with gelatin, preferably mixed with diisocyanate is preferred.

Permeability and strength measurements on expanded prostheses have shown that the bursting strength of the prostheses undergoes no change as a result of the expansion. The water permeability of unimpregnated prostheses increases somewhat as a result of the expansion, the permeability significantly increasing from the small calibre end to the prosthesis centre, but only insignificantly from the prosthesis centre to the expanded end. This is possibly attributable to the fact that the loop structure in the prosthesis wall becomes flatter on expansion, without the pores in the loop structure becoming significantly larger.

We claim:

1. A textile, tubular vessel prosthesis having two ends and a length comprising:

(1) a plurality of yarns or threads having an arrangement that is knitted, a selected glass transition point, and a melting temperature; a first diameter at a first end of the prosthesis; a second diameter at a second end of the prosthesis; with the second diameter being smaller than the first diameter; wherein the prosthesis has a substantially constant number of yarns or threads in cross-section over the entire length and forms a conical shape;

(2) has a tensile strength of the yarns or threads and a bursting pressure which are substantially constant over the length; and (3) exhibits no stretching or elongation of the knitted yarns or threads in the vicinity of the first end compared with the knitted yarns or threads in the vicinity of the second end.

2. The prosthesis according to claim 1, wherein a tubular textile blank having a preselected length and a constant diameter between the length is transformed into the conical shape, with no substantial lengthening of the yarns or threads, and the conical shape is fixed by heating the blank to a temperature above the glass transition point and below the melting range of the yarns or threads, followed by subsequent cooling.

3. The prosthesis according to claim 1, wherein the first end is formed by elastically expanding the tubular blank and expansion is limited to a widening or reorientation of a bond or loop of yarn or thread, without any lengthening or expansion of the yarn or thread.

4. The prosthesis according to claim 1, wherein each diameter is between about 4 mm and 40 mm, the first and second diameters differ by about 10 to 100 percent based on the smaller diameter, and the diameter diverges along the conical shape of the prosthesis by not more than +5 percent from that of a true cone.

* * * * *